(12) United States Patent
Coughlin et al.

(10) Patent No.: US 8,338,456 B2
(45) Date of Patent: Dec. 25, 2012

(54) CUT-POINT IN PTEN PROTEIN EXPRESSION THAT ACCURATELY IDENTIFIES TUMORS AND IS PREDICTIVE OF DRUG RESPONSE TO A PAN-ERBB INHIBITOR

(75) Inventors: Christina Marie Coughlin, Berwyn, PA (US); Jay Marshall Feingold, Wynnewood, PA (US); Daniel Stephen Johnston, Trappe, PA (US); Anna Berkenblit, Needham, MA (US); Andrew Louis Strahs, Maynard, MA (US); Charles Michael Zacharchuk, Westford, MA (US)

(73) Assignee: Wyeth LLC, Madison, NJ (US)

( * ) Notice: Subject to any disclaimer, the term of this patent is extended or adjusted under 35 U.S.C. 154(b) by 81 days.

(21) Appl. No.: 12/984,043

(22) Filed: Jan. 4, 2011

(65) Prior Publication Data

US 2012/0010240 A1    Jan. 12, 2012

Related U.S. Application Data

(60) Provisional application No. 61/294,615, filed on Jan. 13, 2010.

(51) Int. Cl.
*A61K 31/4709* (2006.01)
*A61P 35/00* (2006.01)
*G01N 1/30* (2006.01)
*G01N 33/53* (2006.01)

(52) U.S. Cl. .................... 514/313; 514/506.9; 435/7.41; 435/21

(58) Field of Classification Search .................. 514/313, 514/506.9; 435/7.41, 21
See application file for complete search history.

(56) References Cited

U.S. PATENT DOCUMENTS

| 7,399,865 B2 | 7/2008 | Wissner et al. |
| 2007/0104721 A1 | 5/2007 | Moore et al. |

FOREIGN PATENT DOCUMENTS

| WO | 2005/044091 A2 | 5/2005 |
| WO | 2006/044748 A2 | 4/2006 |
| WO | 2007/137187 A2 | 11/2007 |
| WO | WO 2009/052264 | 4/2009 |
| WO | 2009/108637 A1 | 9/2009 |
| WO | 2010/045318 A2 | 4/2010 |

OTHER PUBLICATIONS

Allegra, C., et al., "American Society of Clinical Oncology Provisional Clinical Opinion: Testing for *KRAS* Gene Mutations in Patients With Metastatic Colorectal Carcinoma to Predict Response to Anti-Epidermal Growth Factor Receptor Monoclonal Antibody Therapy," *Journal of Clinical Oncology*, 2009, vol. 27, No. 12, 2091-2096.

Berns, K., et al., "A Functional Genetic Approach Identifies the PI3K Pathway as a Major Determinant of Trastuzumab Resistance in Breast Cancer," *Cancer Cell*, 2007, vol. 12, 395-402.
Bettendorf, O., et al., "Chromosomal Imbalances, Loss of Heterozygosity, and Immunohistochemical Expression of TP53, RB1, and PTEN in Intraductal Cancer, Intraepithelial Neoplasia, and Invasive Adenocarcinoma of the Prostate," *Genes, Chromosomes & Cancer*, 2008, vol. 47, 565-572.
Bose, S., "Allelic Loss of Chromosome 10q23 is Associated With Tumor Progression in Breast Carcinomas," *Oncogene*, 1998, vol. 17, No. 123-127.
Bose, S., et al., "Reduced Expression of PTEN Correlates With Breast Cancer Progression," *Human Pathology*, 2002, vol. 33, 405-409.
Depowski, P., "Loss of Expression of the PTEN Gene Protein Product is Associated With Poor Outcome in Breast Cancer," *Modern Pathology*, 2001, vol. 14, No. 7, 672-676.
Engelman, J., "Targeting PI3K Signalling in Cancer: Opportunities, Challenges and Limitations," *Nature Reviews of Cancer*, 2009, vol. 9, 550-562.
Hager, M., et al., "PTEN Expression in Renal Cell Carcinoma and Oncocytoma and Prognosis," *Pathology*, 2007, vol. 39, No. 5, 482-485. (Abstract only).
Maehama, T., "PTEN: Its Deregulations and Tumorigenesis," *Biol. Pharm. Bull.*, 2007, vol. 30, 1624-1627.
Nagata, Y., et al., "PTEN Activation Contributes to Tumor Inhibition by Trastuzumab, and Loss of PTEN Predicts Trastuzumab Resistance in Patients," *Cancer Cell*, 2004, vol. 6, 117-127.
Pantuck, A., "Prognostic Relevance of the mTOR Pathway in Renal Cell Carcinoma," *Cancer*, 2007, vol. 109, No. 11, 2257-2267.
Perez-Tenorio, G., et al., PIK3CA Mutations and PTEN Loss Correlate With Similar Prognostic Factors and are not Mutually Exclusive in Breast Cancer, *Clinical Cancer Research*, 2007, vol. 13, No. 3577-3584.
Perren, A., et al., "Immunohistochemical Evidence of Loss of PTEN Expression in Primary Ductal Adenocarcinomas of the Breast," *American Journal of Pathology*, 1999, vol. 155, 1253-1260.
Rubin, M., et al., "10q23.3 Loss of Heterozygosity Is Higher in Lymph Node-Positive (pT2-3,N+) Versus Lymph Node-Negative (pT2-3, N0) Prostate Cancer," *Human Pathology*, 2000, vol. 31, 504-508.
Saal, L., et al., "*PIK3CA* Mutations Correlate With Hormone Receptors, Node Metastasis, and ERBB2, and Are Mutually Exclusive With PTEN Loss in Human Breast Carcinoma," *Cancer Research*, 2005, vol. 65, No. 7, 2554-2559.
Stemke-Hale, K., et al., "An Integrative Genomic and Proteomic Analysis of PIK3Ca, PTEN, and AKT Mutations in Breast Cancer," *Cancer Research*, 2008, vol. 68, No. 15, 6084-6091.
Yim, E., et al., "Rak Functions As a Tumor Suppressor by Regulating PTEN Protein Stability and Function," *Cancer Cell*, 2009, vol. 15, 304-314.
Zhou, J., et al., "Activation of the PTEN/mTOR/STAT3 Pathway in Breast Cancer Stem-like Cells Is Required for Viability and Maintenance," *Proceedings of the National Academy of Science U. S. A.*, 2007, vol. 104, No. 4 116158-16163.

*Primary Examiner* — Raymond Henley, III

(74) *Attorney, Agent, or Firm* — Jones Day

(57) ABSTRACT

A cut-point in the quantitative measurement of PTEN protein expression that accurately identifies tumors with two inactivated alleles of the PTEN gene. Patients with a normalized PTEN score of PTEN null will be treated with a pan-ErbB tyrosine kinase inhibitor. A normalized PTEN protein expression score is obtained by comparing the tumor PTEN OD expression value with the non-malignant PTEN OD expression value.

20 Claims, No Drawings

CUT-POINT IN PTEN PROTEIN EXPRESSION THAT ACCURATELY IDENTIFIES TUMORS AND IS PREDICTIVE OF DRUG RESPONSE TO A PAN-ERBB INHIBITOR

CROSS-REFERENCE TO RELATED APPLICATIONS

This application claims the benefit of U.S. Provisional Application Ser. No. 61/294,615, filed Jan. 13, 2010, which is incorporated by reference in its entirety.

FIELD OF THE INVENTION

The present invention relates to methods for treating breast cancer. In particular, the present invention is related to methods of treating breast cancer patients with a pan-ErbB tyrosine kinase inhibitor. More particularly, the invention discloses a cut-point in a quantitative immunohistochemical assay for PTEN protein expression that accurately identifies tumors with two inactivated alleles of the PTEN gene in human tumor biopsy samples and which is predictive of drug response to a pan-ErbB inhibitor.

BACKGROUND

The tumor suppressor PTEN is a dual-specificity phosphatase (lipid and protein) that functions as a check (or the "brakes") on the PI3K signaling complex. PTEN mediates the dephosphorylation of phosphatidylinositol-triphosphate ($PIP_3$) to phosphatidylinositol-diphosphate ($PIP_2$), eliminating the membrane binding site for 3-Phosphoinositide-Dependent Kinase-1 (PDK1) and Akt/protein kinase B (PKB) and thus antagonizing the activity of PI3K. The PTEN gene (at locus 10q23) is inactivated in a number of human malignancies, including breast, brain, endometrial, kidney, and prostate cancers. The inactivation of PTEN correlates with disease progression and poor prognosis, suggesting a key role in oncogenesis (Bose S, et al (2002) Reduced expression of PTEN correlates with breast cancer progression. Hum. Pathol. 33:405-409; Rubin M A, et al (2000) 10q23.3 loss of heterozygosity is higher in lymph node-positive (pT2-3,N+) versus lymph node-negative (pT2-3,N0) prostate cancer, Hum. Pathol. 31:504-508, and Depowski P L, Rosenthal S I, Ross J S (2001) Loss of expression of the PTEN gene protein product is associated with poor outcome in breast cancer. Mod. Pathol. 14:672-676).

In experimental systems, inactivation of PTEN has been shown to lead to unchecked activation of Akt/PKB. Unchecked Akt/PKB activity leads to inhibition of apoptosis, cellular growth, and enhanced proliferation, and subsequently to an oncogenic phenotype. Restoration of PTEN expression in PTEN-null systems leads to loss of the oncogenic phenotype.

In breast cancer, multiple mechanisms of PTEN loss of function have been demonstrated, including mutations, gene deletions, and transcriptional downregulation via miRNA or epigenetic silencing. Most of these mechanisms of inactivation lead to a significant reduction in the amount of the PTEN protein that is produced in the tumor cells. In tumors harboring such mechanisms of inactivation, a reduction in PTEN protein levels in breast cancer has been observed using various protein measurements, including one standard method used in diagnostics, immunohistochemistry (IHC). Using IHC, various studies have reported reduced PTEN in 15% to 48% of patients. The spectrum of PTEN mutations, gene deletions, and epigenetic events as mechanisms of inactivation present an interesting study of tumor biology, and the variable combinations of these inactivation mechanisms are likely to contribute to the heterogeneity in published literature on the reduction in PTEN expression observed. Mutations in the PTEN gene are quite common in malignancies, such as endometrial carcinoma and glioblastoma; however, such mutations are relatively rare in breast cancer. Mutations in the PTEN gene are found in approximately 5% of patients and most represent frame shift mutations that can lead to a destabilized protein. In contrast, the major mechanism of PTEN inactivation in breast cancer appears to be PTEN gene deletion. Multiple additional mechanisms of PTEN loss beyond gene loss or mutations have been identified. At the transcriptional level, epigenetic silencing via promoter methylation or miRNA expression (e.g., miR-21) have been described. Further mechanisms to reduce PTEN expression involve loss of stabilizing proteins, such as Rak, which phosphorylates PTEN, thus protecting it from ubiquitin-mediated degradation.

Multiple approaches to PTEN IHC have been published with the attempt to correlate to drug response (See for example, Berns K et al. (2007) A functional genetic approach identifies the PI3K pathway as a major determinant of trastuzumab resistance in breast cancer; Cancer Cell 12:395-402; and Nagata Y et al (2004) PTEN activation contributes to tumor inhibition by trastuzumab, and loss of PTEN predicts trastuzumab resistance in patients; Cancer Cell 6:117-127).

SUMMARY OF THE INVENTION

In the present disclosure a cut-point in PTEN protein expression is identified using quantitative results. This cut-point will accurately allow for the identification of patients who will benefit from pan-ErbB inhibitor therapy. The cut-point accurately identifies tumors with two inactivated alleles of the PTEN gene in human tumor biopsy samples and is predictive of drug response to a pan-ErbB inhibitor.

In an embodiment, the invention relates to a method for determining to treat a breast cancer patient. The method comprises obtaining a tumor cell and a non-tumorgenic cell from the patient; determining a quantitative measure of PTEN protein expression in the tumor cell and in the non-tumorgenic cell; and calculating a normalized PTEN protein expression score by comparing these two quantitative measures of PTEN protein expression. The patient is treated with a pan-ErbB tyrosine kinase inhibitor if the normalized PTEN protein expression score is PTEN null. In some embodiments of the invention, the non-tumorgenic cell is a stroma cell or an endothelial cell. In some embodiments of the invention the tumor cell and the non-tumorgenic cell are from the same sample.

In some embodiments of the invention the pan-ErbB tyrosine kinase inhibitor prevents binding of PIK3CA to the intracellular portion of ErbB in an irreversible manner. In particular embodiments of the invention, the pan-ErbB tyrosine kinase inhibitor is neratinib. In some embodiments of the invention, the quantitative measure of PTEN protein expression comprises one or more of: reverse phase protein array, western blot, semi-quantitative or quantitative immunohistochemistry (IHC). In particular embodiments of the invention, the quantitative measure of PTEN protein expression comprises IHC.

In some embodiments, the method of the invention comprises determining a quantitative measure of PTEN protein expression which comprises staining the tumor cell and the non-tumorgenic cell. In some embodiments of the invention, determining a quantitative measure of PTEN protein expression further comprises obtaining a digital image of the stained cells. In particular embodiments of the invention, the PTEN null score is less than 0.15.

In an embodiment, the invention relates to a method of treating cancer in a patient. The method comprises obtaining a tumor cell and a non-tumorgenic cell from the patient; determining a quantitative measure of PTEN protein expression in the tumor cell and in the non-tumorgenic cell; and calculating a normalized PTEN protein expression score by comparing these quantitative measures of PTEN protein expression. The patient is treated with a pan-ErbB tyrosine kinase inhibitor if the normalized PTEN protein expression score is PTEN null.

DETAILED DESCRIPTION

The disclosure provides a cut-point, identified using quantitative results, that accurately allows for the identification of patients who will benefit from pan-ErbB tyrosine kinase inhibitor therapy. In an embodiment, the quantitative results are obtained by using IHC. Patients with a normalized PTEN score of less than 0.15 (defined as "PTEN null") will be treated with pan-ErbB tyrosine kinase inhibitor therapy. In an embodiment, the normalized PTEN score is calculated by dividing the tumor PTEN optical density (OD) expression value by the non-malignant tissue PTEN OD expression value.

In an embodiment, the method comprises generating two PTEN OD expression values using digital imaging, one value for tumor cells and one value for non-malignant cells. The non-malignant cells (e.g. stromal cells or endothelial cells) and the tumor cells may be contained in the same tissue section. The overall normalized PTEN score is computed as the ratio of the PTEN OD expression value obtained for the tumor cells divided by the PTEN OD expression value obtained for normal, non-malignant cells. The cut point defined by the invention allows each patient sample to be identified as PTEN off (with a normalized PTEN score of 0), PTEN reduced (with a normalized PTEN score >0 but less than 0.15) and PTEN ON (with a normalized PTEN score equal to or more than 0.15).

A patient with a normalized PTEN score falling into the category of either PTEN off (score of 0) or PTEN reduced (with a normalized score greater than 0 but less than 0.15) will be defined as "PTEN null," and the patient will be treated with a pan-ErbB tyrosine kinase inhibitor. If the normalized PTEN score is PTEN ON, the patient may be treated with trastuzumab. In some embodiments of the invention, the PTEN OD expression value is less than 15% of the normal tissue OD expression value, leading to a normalized PTEN score of less than 0.15 and a designation of PTEN reduced.

Classification of tumors according to, e.g., mutation analysis, DNA copy number, methylation status, and patterns of gene or protein expression are available. Since the approval of trastuzumab, nearly half of all new compounds approved by the U.S. Food and Drug Administration to treat tumors have been associated with some form of patient selection biomarker. These examples primarily focus on measuring target biology in tumor samples. A more recent development in patient selection is the identification of drug resistance mechanisms in an effort to distinguish those patients who will achieve clinical benefit from a specific agent from those who will not. For example, V-Ki-ras2 Kirsten rat sarcoma [KRAS] mutation status identifies those patients who will not benefit from the addition of antibody-based epidermal growth factor receptor (EGFR) inhibitors in colon cancer (Allegra C J, Jessup J M, Somerfield M R et al (2009) American Society of Clinical Oncology provisional clinical opinion: testing for KRAS gene mutations in patients with metastatic colorectal carcinoma to predict response to anti-epidermal growth factor receptor monoclonal antibody therapy. J. Clin. Oncol. 27:2091-2096.)

Members of the ErbB RTK family (EGFR, HER2, HER3, HER4) undergo genetic events leading to signaling activation in multiple human cancer types; those most often noted in breast cancer include amplifications, mutations, and intronic repeats with a role in transcriptional activation. PI3K is one of several signaling cascades engaged by the oncogenic RTK complexes at the membrane and may represent a key therapeutic target (recently reviewed by Engelman J A (2009) Targeting PI3K signalling in cancer: opportunities, challenges and limitations. Nat. Rev. Cancer 9:550-562). The critical role of this signaling node in cancer is highlighted by the proportion of human malignancies with genetic lesions in genes encoding the components of the cascade, namely PIK3CA, PTEN, PDK1, and AKT.

Genetic lesions that lead to constitutive pathway activation in various tumors are on opposite fronts. For example, gain-of-function or activating mutations in or amplification of the p110α subunit of the PIK3CA gene are observed in some tumors and act as the "accelerators" of the signaling cascade, whereas loss-of-function events (i.e., deletion, promoter methylation, or mutations) are generally seen for PTEN and act as the "brakes" on the system.

Current therapeutic approaches in breast cancer that target this pathway include ErbB pathway inhibitors (e.g., trastuzumab, lapatinib, neratinib, BIBW2992), PI3K inhibitors (e.g., XL147, PX-866), mTOR inhibitors (e.g., temsirolimus, everolimus), and dual PI3K-mTOR inhibitors (e.g., BEZ235). The activation of the PI3K pathway has been associated with resistance to ErbB2-targeted therapy in breast cancer, as well as resistance to cytotoxics. Given that multiple therapeutic options exist and that PI3K activity predicts drug resistance in many settings, the question arises as to whether assays can be developed that allow for the prediction of "PI3K pathway activation" in preserved human tumor tissue samples for clinical development.

Neratinib (also called HKI-272) inhibits phosphorylation of the ErbB receptors and downstream substrates; due to this activity in preclinical models, neratinib has been shown to inhibit phosphorylation and activation of the PI3K complex. See, e.g., pages 6-7 of PCT publication No. WO09/052264; paragraphs 7 and 21 of U.S. patent application publication No. US20070104721; and U.S. Pat. No. 7,399,865.

A decrease in PTEN protein expression has been associated with resistance to treatment of Her2+ breast cancer with trastuzumab. Using a semiquantitative immunohistochemistry (IHC) assay, these changes have been associated with trastuzumab resistance in breast cancer (see Berns K, et al. (2007) Cancer Cell (4):395-402).

Loss of PTEN has been routinely studied in the clinic using standard IHC approaches, typically with an antibody that recognizes a C-terminal protein epitope. Using an antibody directed against the C-terminal end of the protein will result in little to no signal generated in tumors harboring mutations that produce truncated forms of the protein. Various examples of concordance versus discordance between known genetic loss events and the expression of PTEN via IHC exist in the literature; this can lead to some challenges in the interpretation of the underlying biology (Bose S, et al. (2002) Reduced expression of PTEN correlates with breast cancer progression, Hum. Pathol. 33:405-409, and Bettendorf O, et al. (2008) Chromosomal imbalances, loss of heterozygosity, and immunohistochemical expression of TP53, RB1, and PTEN in intraductal cancer, intraepithelial neoplasia, and invasive adenocarcinoma of the prostate, Genes Chromosomes Cancer 47:565-572). Several potential explanations exist for the discordance between the percentage of patients with genetic lesions and that with decreased protein levels. Without being bound by theory, IHC methods can be qualitative or semi-quantitative and differences in interpretation can lead to different results. IHC methods detect all species of the full-length protein (functional or dysfunctional) and "low" protein levels may derive from either destabilizing mutations, miRNA expression, or co-expressed stabilizing proteins, whereas a full complement of the PTEN protein can be observed with a point mutation in the phosphatase domain (Maehama T (2007) PTEN: its deregulation and tumorigenesis. Biol. Pharm. Bull. 30:1624-1627, and—Yim E K, Peng G, Dai H et al (2009) Rak functions as a tumor suppressor by regulating PTEN protein stability and function, Cancer Cell 15:304-314).

In some embodiments, neratinib is administered to a subject at a dose between 100 and 500 mg per day, between 200 and 400 mg per day, and at a dose of about 250 mg per day.

In some embodiments, the invention provides a method of treating breast cancer with neratinib in conjunction with another treatment for breast cancer. Additional treatment or treatments can include surgery, radiation or additional chemotherapy agents selected from one or more of the following: aromatase inhibitors, including letrozole (Femara), anastrazole (Arimidex) and exemestane (Aromasin); goserelin (Zoladex); anthracyclines, including doxorubicin (Adriamycin), epirubicin (Ellence), and liposomal doxorubicin (Doxil); taxanes, including docetaxel (Taxotere), paclitaxel (Taxol), and protein-bound paclitaxel (Abraxane), Cyclophosphamide (Cytoxan); Capecitabine (Xeloda) and 5 fluorouracil (5 FU); Vinorelbine (Navelbine); Gemcitabine (Gemzar); and Trastuzumab (Herceptin).

The term "treating," as used herein, unless otherwise indicated, means reversing, alleviating, or inhibiting the progress of the disorder or condition to which such term applies, or one or more symptoms of such disorder or condition. The terms "therapy" and "treatment", as used herein, unless otherwise indicated, refer to the act of treating as "treating" is defined immediately above. As used herein, "subject" and "patient" are used interchangeably.

"Non-malignant" and "non-tumorgenic" are used interchangeably herein.

In an embodiment, standard IHC methods are used to stain tumors for PTEN protein expression. Digital images are obtained and OD numeric values for both normal tissue (e.g. stromal or endothelial cell) PTEN expression, as well as tumor PTEN compartments are obtained. The sample's normalized PTEN score is calculated as tumor PTEN OD expression value divided by the normal (or non-malignant) tissue PTEN OD expression value. This process of normalization of the tumor-specific PTEN OD to the normal, non-malignant tissue OD allows for correction in staining differences using the internal control of non-malignant tissue staining for each sample.

A decrease in the normalized PTEN score means a decrease of PTEN protein levels as compared to levels of PTEN protein seen in normal, non-malignant or non-tumorgenic cells. (e.g. stromal or endothelial cells). The stromal or endothelial cells may be present in the same tissue section as the tumor cells.

"Neratinib" is an orally available, 6,7-disubstituted-4-anilinoquinoline-3-carbonitrile irreversible inhibitor of the HER-2 receptor tyrosine kinase with potential antineoplastic activity. Neratinib binds to the HER-2 receptor irreversibly, thereby reducing autophosphorylation in cells, apparently by targeting a cysteine residue in the ATP-binding pocket of the receptor. Treatment of cells with this agent results in inhibition of downstream signal transduction events and cell cycle regulatory pathways; arrest at the G1-S (Gap 1/DNA synthesis)-phase transition of the cell division cycle; and ultimately decreased cellular proliferation. Neratinib also inhibits the epidermal growth factor receptor (EGFR) kinase and the proliferation of EGFR-dependent cells.

"Trastuzumab" and "Herceptin" refer to a monoclonal antibody that binds to the external membrane domain of the HER2/Neu receptor. The ErbB/HER receptors are proteins that are embedded in the cell membrane and communicate molecular signals from outside the cell to inside the cell, and turn genes on and off. The ErbB/HER proteins regulate cell growth, survival, adhesion, migration, and differentiation functions that are amplified or weakened in cancer cells.

Quantitative immunohistochemistry is used to assess the protein expression of the PTEN protein in preserved human tumor samples of patients. PTEN protein levels are measured using digital imaging systems that are able to quantitate protein expression levels (e.g. such as the Aperio Digital Pathology Environment (Vista, Calif.) or Automated Quantitative Analysis (AQUA; HistoRx, New Haven, Conn.). These systems for image analysis use pixels to determine the quantitative IHC numeric value for the OD of the cells that are selected for analysis.

A "normalized PTEN score" is defined as the ratio of PTEN protein expression in a tumor tissue sample divided by the PTEN protein expression in a non-tumorgenic tissue sample. Non-tumorgenic tissue samples and tumor tissue samples may be found in the same breast tissue section.

The "PTEN score" is calculated as the ratio of the PTEN tumor cell OD expression value, normalized to (divided by) the normal tissue PTEN OD expression value. Normal tissue expression can be defined as PTEN OD expression value measured in stromal cells or endothelial cells (or any other normal tissue cells that are stained). Non-tumorgenic tissue cells and tumor tissue cells may be stained in the same tissue section.

As used herein, normalized PTEN scores may be defined as PTEN null or PTEN ON. PTEN null comprises the group of patients with PTEN scores of PTEN off and PTEN reduced. A PTEN score of PTEN off corresponds to a tissue sample with no detectable PTEN protein expression (PTEN OD expression value of 0). This tissue sample will have a normalized PTEN score of 0. A PTEN score of PTEN reduced corresponds to a tissue sample with a detectable range of PTEN protein expression (i.e., the tumor PTEN OD expression value is >0 but less than 15% of the total score for non-tumorgenic tissue). In an embodiment, the designation of PTEN reduced results when a patient sample demonstrates a normalized PTEN score of more than 0 but less than 0.15. In an embodiment, the designation of PTEN reduced results from patient sample with a normalized PTEN score of more than 0 but less than equal to 0.10. A normalized PTEN score equal to or greater than 0.15 corresponds to PTEN ON. A PTEN ON designation is defined as a PTEN score where at least one functional, normal PTEN allele is detected in genetic assays. A PTEN null score is a normalized PTEN score of less than 0.15. The PTEN null score may be any number between 0 and 0.15, for example 0.1, 0.11, 0.12, 0.13, 0.14, or any portion thereof.

As used in the specification and claims, the singular form "a", "an", and "the" include plural references unless the context clearly dictates otherwise. For example, the term "a cell" includes a plurality of cells, including mixtures thereof.

PTEN tumor expression OD values generally range from 0 to 30 (using the digital imaging and OD). In an embodiment, using standard, semi-quantitative IHC methods, a 3+ intensity (or very high score) is generally represented by expression OD values of 20 or greater. A mid-range expression OD value generally would be 5-20 (generally 1+ to 2+ intensity using semi-quantitative methods) and low from 0-5 (likely representing a mix of 0 and 1+ intensity using standard semi-quantitative IHC). All of these OD expression values are then normalized to a PTEN "normal tissue" OD expression value generally in the 20-25 range in the current assay being used which is a standard IHC brown stain with the Aperio digital imaging system. The Aperio digital imaging system generates an optical density (OD) for the tissue and staining parameter selected.

A cut-point in the normalized PTEN score that identifies the "PTEN null" group of tumors reliably selects those tumors with no functional PTEN protein. This cut-point will be determined as that normalized PTEN expression score that reliably identifies those tumor samples from patients with dysregulation to both of the PTEN alleles. Furthermore, the patients with tumors that fall into the "PTEN null" group are predicted to be those with superior clinical response to a pan-ErbB inhibitor.

Prior semiquantitative approaches have divided patients into multiple segments based on immunohistochemical PTEN staining. Most of these studies have not found that the various levels of PTEN observed in patients' tumor samples correlate with drug response. Different results have been demonstrated with respect to prognostic information provided by the PTEN stain in renal cancer. See for example, Pantuck A J et al. (2007) Prognostic relevance of the mTOR pathway in renal cell carcinoma: implications for molecular patient selection for targeted therapy, Cancer 109(11):2257-2267; and Hager M et al. (2007) PTEN expression in renal cell carcinoma and oncocytoma and prognosis, Pathology 39(5):482-485.

Two PTEN alleles exist at the 10q23 locus. In many tumors, both loci are affected by one of several mechanisms of inactivation such as promoter methylation, gene deletion, or mutation. A cut-point in the PTEN protein expression will be determined that reliably identifies those tumors with hits to both of the PTEN gene alleles and thus, minimal to no functional PTEN protein.

In breast cancer, multiple mechanisms of PTEN loss of function have been demonstrated, including mutations, gene deletions, and transcriptional downregulation via miRNA or epigenetic silencing. Reduction in PTEN protein levels in breast cancer is observed using immunohistochemistry (IHC); various studies have reported reduced PTEN in 15% to 48% of patients (Depowski P L, Rosenthal S I, and Ross J S (2001) Loss of expression of the PTEN gene protein product is associated with poor outcome in breast cancer, Mod. Pathol. 14:672-676; Bose S, et al (1998) Allelic loss of chromosome 10q23 is associated with tumor progression in breast carcinomas, Oncogene 17:123-127.34; Perez-Tenorio G, et al (2007) PIK3CA mutations and PTEN loss correlate with similar prognostic factors and are not mutually exclusive in breast cancer, Clin. Cancer Res. 13:3577-3584; Saal L H, et al (2005) PIK3CA mutations correlate with hormone receptors, node metastasis, and ERBB2, and are mutually exclusive with PTEN loss in human breast carcinoma, Cancer Res. 65:2554-2559; and Perren A, et al (1999) Immunohistochemical evidence of loss of PTEN expression in primary ductal adenocarcinomas of the breast. Am. J. Pathol. 155: 1253-1260).

The spectrum of PTEN mutations, gene deletions, and epigenetic events as mechanisms of inactivation present an interesting study of tumor biology, and the variable combinations of these inactivation mechanisms are likely to contribute to the heterogeneity in published literature on the reduction in PTEN expression observed. Mutations in the PTEN gene are quite common in malignancies, such as endometrial carcinoma and glioblastoma; however, such mutations are found in only approximately 5% of breast cancer patients. Most of these mutations represent frame shift mutations, which if the gene retains the capacity to be translated, often leads to a destabilized protein. In contrast, the major mechanism of PTEN inactivation in breast cancer appears to be PTEN gene deletion. Multiple additional mechanisms of PTEN loss beyond gene loss or mutations have been identified, which often represent the mechanism of dysregulation of the second, non-deleted allele in tumors. At the transcriptional level, epigenetic silencing via promoter methylation or miRNA expression (e.g., miR-21) has been described. Further mechanisms to reduce PTEN expression involve loss of stabilizing proteins, such as Rak, which phosphorylates PTEN, thus protecting it from ubiquitin-mediated degradation.

Alternative methods to evaluate PTEN protein expression are contemplated for use in the practice of the invention. Quantitative methods, such as reverse-phase protein microarray technology or a quantitative IHC method, can allow detection of minor changes in protein levels that are not detected by standard IHC. These methods have shown a better concordance between interpretation of PTEN protein levels and genetics (Yim E K, et al (2009) Rak functions as a tumor suppressor by regulating PTEN protein stability and function, Cancer Cell 15:304-314; Stemke-Hale K, et al (2008) An integrative genomic and proteomic analysis of PIK3CA, PTEN, and AKT mutations in breast cancer, Cancer Res. 68:6084-6091; Zhou J, et al (2007) Activation of the PTEN/mTOR/STAT3 pathway in breast cancer stem-like cells is required for viability and maintenance, Proc. Natl. Acad. Sci. U.S.A. 104:16158-16163). These novel quantitative protein measurements are applicable in preserved samples and such assays are potentially more reliable in studying the underlying pathway biology compared with standard IHC. Alternative quantitative methods such as the RPPA will also require the development of the cut-point for PTEN protein expression score.

EXAMPLES

Example 1

The present invention relates to methods of determining the treatment of a breast cancer patient. A whole tissue section is obtained from a patient and stained using immunohistochemistry (IHC), for PTEN protein expression using an antibody that recognizes the C-terminal domain of the protein. A digital image of the stained tissue is obtained to identify tumor cells and normal tissue cells in the sample. The tumor cell expression OD value is obtained and the normal, non-malignant expression OD value is obtained. A comparison of the PTEN protein expression OD in tumor cells with PTEN protein expression OD in normal tissue cells provides a normalized PTEN score (PTEN tumor cell OD/PTEN normal tissue OD).

Normalized PTEN scores generally will range from 0 to 1. Based on the normalized PTEN scores, the patient is classified as PTEN off, PTEN reduced, or PTEN ON. Patients with a normalized PTEN score of 0 are placed into the category of PTEN off. The clinical designation of "PTEN null" includes those patients with no PTEN protein expression and those patients with a PTEN protein expression OD value so low that it is not detectable by IHC (normalized PTEN score of 0 or PTEN off). Patients with a normalized PTEN score of greater than 0 but less than 0.15 (or having a PTEN tumor expression OD value which is less than 15% of the normal tissue expression OD value) are placed into the classification of PTEN reduced. The PTEN off and PTEN reduced groups both correlate with an almost complete loss of PTEN gene function via hits to the two PTEN gene alleles. Proper function of at least one of the PTEN alleles produces a normalized score of at least 0.15. Patients with a normalized PTEN score of at least 0.15 are placed into the classification of PTEN ON.

Patients identified as "PTEN null" (in the category of either PTEN off or PTEN reduced, or having a normalized PTEN score of less than 0.15) are treated with neratinib and patients identified as PTEN ON may be treated with a different therapy.

All publications and patent applications mentioned in the specification are indicative of the level of those skilled in the art to which this invention pertains. All publications and patent applications mentioned in the specification are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A method for determining the treatment for a breast cancer patient comprising:
    obtaining a tumor cell and a non-tumorgenic cell from the patient;
    determining a quantitative measure of PTEN protein expression in the tumor cell and the non-tumorgenic cell;
    calculating a normalized PTEN protein expression score by comparing the quantitative measure of PTEN protein expression in the tumor cell with the quantitative measure of PTEN protein expression in the non-tumorgenic cell; and
    determining to treat the patient with a pan-ErbB tyrosine kinase inhibitor if the normalized PTEN protein expression score is PTEN null.

2. The method of claim 1, wherein the non-tumorgenic cell is a stroma cell or an endothelial cell.

3. The method of claim 1, wherein the tumor cell and the non-tumorgenic cell are from the same sample.

4. The method of claim 1, wherein the pan-ErbB tyrosine kinase inhibitor prevents binding of PIK3CA to the intracellular portion of ErbB in an irreversible manner.

5. The method of claim 1, wherein the pan-ErbB tyrosine kinase inhibitor is neratinib.

6. The method of any of claim 1, wherein the quantitative measure of PTEN protein expression comprises one or more of: reverse phase protein array, western blot, semi-quantitative or quantitative immunohistochemistry (IHC).

7. The method of claim 6, wherein the tumor cell and the non-tumorgenic cell are from the same sample.

8. The method of claim 1, wherein determining a quantitative measure of PTEN protein expression comprises staining the tumor cell and the non-tumorgenic cell, and wherein said determination of a quantitative measure of PTEN protein expression optionally comprises obtaining a digital image of the stained cells.

9. The method of claim 1, wherein the normalized PTEN null score is less than 0.15.

10. The method of claim 1, wherein the quantitative measure of PTEN protein expression is a PTEN optical density expression value.

11. A method for treating cancer in a patient comprising:
    obtaining a tumor cell and a non-tumorgenic cell from the patient;
    determining a quantitative measure of PTEN protein expression in the tumor cell;
    calculating a normalized PTEN protein expression score by comparing the quantitative measure of PTEN protein expression in the tumor cell with a quantitative measure of PTEN protein expression in the non-tumorgenic cell; and
    treating the patient with a pan-ErbB tyrosine kinase inhibitor if the normalized PTEN protein expression score is PTEN null.

12. The method of claim 11, wherein the non-tumorgenic cell is a stroma cell or an endothelial cell.

13. The method of claim 11, wherein the tumor cell and the non-tumorgenic cell are from the same sample.

14. The method of any one of claim 11, wherein the pan-ErbB tyrosine kinase inhibitor prevents binding of PIK3CA to the intracellular portion of ErbB in an irreversible manner.

15. The method of claim 11, wherein the pan-ErbB tyrosine kinase inhibitor is neratinib.

16. The method of any one of claim 11, wherein the quantitative measure of PTEN protein expression comprises one or more of: reverse phase protein array, western blot, semi-quantitative or quantitative immunohistochemistry (IHC).

17. The method of claim 16, wherein the tumor cell and the non-tumorgenic cell are from the same sample.

18. The method of claim 11, wherein determining a quantitative measure of PTEN protein expression comprises staining the tumor cell and the non-tumorgenic cell, and wherein said determination of a quantitative measure of PTEN protein expression optionally comprises obtaining a digital image of the stained cells.

19. The method of claim 11, wherein the normalized PTEN null score comprises any score of less than 0.15.

20. The method of claim 11, wherein the quantitative measure of PTEN protein expression is a PTEN optical density expression value.

* * * * *